United States Patent [19]

Sugano et al.

[11] Patent Number: 4,665,056

[45] Date of Patent: May 12, 1987

[54] DIHYDROOROTIC ACID DERIVATIVE AND PROCESSES FOR PREPARING THE SAME

[75] Inventors: Hiroshi Sugano, Nara; Ryuichi Ishida, Suita; Michio Yamamura, Tondabayashi, all of Japan

[73] Assignee: Tanabe Seiyaku Co., Ltd., Osaka, Japan

[21] Appl. No.: 749,202

[22] Filed: Jun. 27, 1985

[30] Foreign Application Priority Data

Jul. 10, 1984 [GB] United Kingdom ............ 8417541
Apr. 18, 1985 [GB] United Kingdom ............ 8509929

[51] Int. Cl.$^4$ .................. A61K 37/43; C07K 5/08
[52] U.S. Cl. .................................... 514/18; 530/331
[58] Field of Search ............. 530/331; 260/998.2; 514/18

[56] References Cited

U.S. PATENT DOCUMENTS

| | | | |
|---|---|---|---|
| 3,753,969 | 8/1973 | Folkers et al. | 530/331 |
| 3,757,003 | 9/1973 | Folkers et al. | 530/331 |
| 4,045,556 | 8/1977 | Schwertner et al. | 260/998.2 |
| 4,100,152 | 7/1978 | Fujino et al. | 530/331 |
| 4,260,601 | 4/1981 | Reichelt et al. | 530/331 |

*Primary Examiner*—Delbert R. Phillips
*Attorney, Agent, or Firm*—Birch, Stewart, Kolasch & Birch

[57] ABSTRACT

There are disclosed 1-methyl-4,5-dihydroorotyl-histidylprolinamide or a pharmaceutically acceptable acid addition salt thereof, processes for their preparation and pharmaceutical compositions containing them. The prolinamide and the pharmaceutically acceptable acid addition salts thereof are useful for the treatment of central nervous system disorder.

6 Claims, No Drawings

DIHYDROOROTIC ACID DERIVATIVE AND PROCESSES FOR PREPARING THE SAME

This invention relates to a novel 1-methyl-4,5-dihydroorotic acid derivative, a process for preparing the same and a pharmaceutical composition thereof. More particularly, it relates to 1-methyl-4,5-dihydroorotyl-histidyl-prolinamide of the formula:

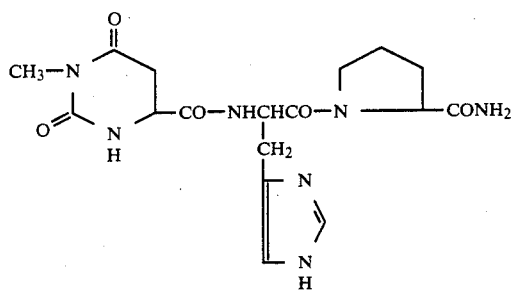

or a pharmaceutically acceptable acid addition salt thereof.

It is known that TRH (i.e., thyrotropin releasing hormone; L-pyroglutamyl-L-histidyl-L-prolinamide) is useful as a medicine for treating consciousness disorders due to a brain dysfunction; but at the same time it possesses the TSH (thyroid stimulating hormone)-releasing activity, which is considered to be an undesirable action for its therapeutic effect on the consciousness disorders. In this connection, U.S. Pat. Nos. 4,100,152 and 4,045,556 disclose that (2,3,4,5-tetrahydro-2-oxo-L-5-furancarbonyl)-L-histidyl-L-prolinamide and orotyl-L-histidyl-L-prolinamide show the therapeutic effect on said consciousness disorders with less side effects as compared with TRH.

As a result of various investigations, we have now found that the compound (I) of the present invention is useful as a medicine for treatment or prophylaxis of central nervous system disorders (e.g., consciousness disorder). Namely, the compound (I) of the invention is quite characteristic in that it shows much stronger activating effects upon central nervous system (e.g., antagonistic effect on pentobarbital anesthesia, increasing effect on spontaneous locomotor activity, antagonistic effect on reserpine-induced hypothermia, potentiating effect on action of L-Dopa) with relatively less side effects (e.g., TSH-releasing activity) as compared with TRH and its derivatives mentioned above.

According to the present invention, the compound (I) or a pharmaceutically acceptable acid addition salt thereof can be prepared by the step or steps of:

(A) condensing a 1-methyl-4,5-dihydroorotic acid compound of the formula:

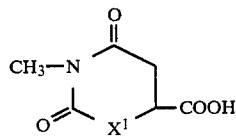

wherein $X^1$ is imino group or a protected imino group, or a reactive derivative thereof with a histidyl-prolinamide compound of the formula:

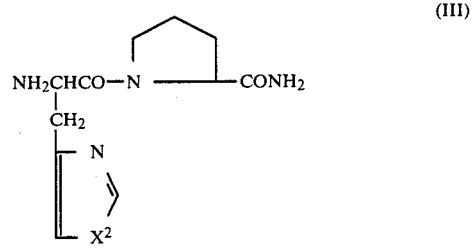

wherein $X^2$ is imino group or a protected imino group, or a salt thereof, (B) condensing a 1-methyl-4,5-dihydroorotyl-histidine compound of the formula:

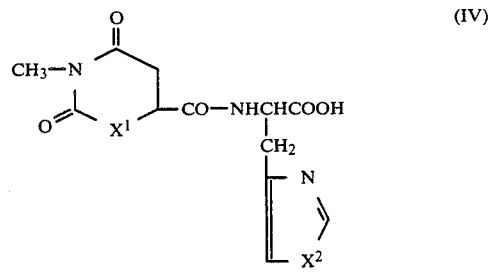

wherein $X^1$ and $X^2$ are the same as defined above, a salt thereof or a reactive derivative thereof with prolinamide of the formula:

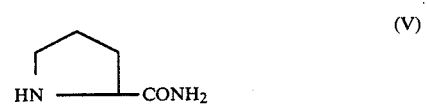

or a salt thereof, or (C) converting an 1-methyl-4,5-dihydroorotyl-histidyl-proline compound of the formula:

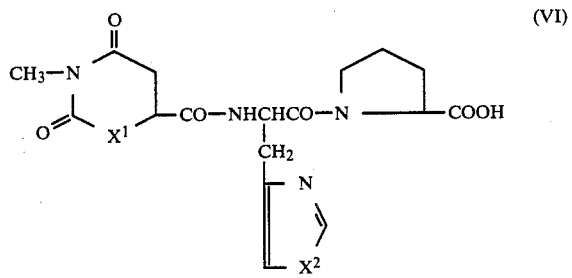

wherein $X^1$ and $X^2$ are the same as defined above, a salt thereof or a reactive derivative thereof into the corresponding amide thereof, (D) when $X^1$ and/or $X^2$ of the product obtained in the reaction step (A), (B) or (C) is (or are) the protected imino group or groups, further removing the protecting group or groups therefrom, and (E) if required, further converting the product into a pharmaceutically acceptable acid addition salt thereof.

The starting compounds (III)–(VI) may be used either in free form or in the form of a salt thereof. Examples of the salt of the compounds (III)–(VI) include inorganic acid addition salts such as hydrochloride, hydrobromide, sulfate or nitrate, organic acid addition salts such as tosylate, methanesulfonate or trifluoroacetate, and so forth.

Suitable examples of the reactive derivative of the compound (II), (IV) or (VI) include the corresponding acid halides (e.g., chloride, bromide), mixed anhydrides (e.g., a mixed anhydride with alkyl carbonate), active esters (e.g., ester with pentachlorophenol, p-nitrophenol, 2,4-dinitrophenol, N-hydroxy-succinimide, N-hydroxyphthalimide, 1-hydroxybenzotriazole or 1-hyroxy-2-pyrrolidon), acid azide and other reactive derivatives such as amide with imidazole, 4-substituted-imidazole or triazole. Esters such as alkyl esters (e.g., methyl or ethyl ester) and aralkyl esters (e.g., benzyl ester) may also be used as the reactive derivative of the compound (VI).

On the other hand, a wide variety of protecting groups which have been usually employed to protect imino group or groups in the peptide synthesis can be used as the protecting group or groups ($X^1$ and/or $X^2$). Examples of such protecting groups $X^1$ and $X^2$ include lower alkanoyl such as formyl, acetyl and propionyl; substituted or unsubstituted benzoyl such as benzoyl; lower alkoxycarbonyl such as methoxycarbonyl, ethoxycarbonyl and tert-butoxycarbonyl; mono-, di- or trihalogeno-lower alkoxycarbonyl such as 2,2,2-trichloroethoxycarbonyl; substituted or unsubstituted benzyloxycarbonyl such as benzyloxycarbonyl and p-methoxybenzyloxycarbonyl; substituted or unsubstituted phenyl-lower alkyl such as benzyl, p-methoxybenzyl and 3,4-dimethoxy-benzyl; and di- or triphenyl-lower alkyl such as benzhydryl and trityl; substituted or unsubstituted phenylsulfonyl such as tosyl; and substituted or unsubstituted phenylsulfenyl such as o-nitrophenylsulfenyl.

[Reaction Steps (A) and (B)]

The condensation of the compound (II) or a reactive derivative thereof with the compound (III) or a salt thereof and the condensation of the compound (IV), a salt thereof or a reactive derivative thereof with the compound (V) or a salt thereof can be accomplished in conventional manners for the synthesis of peptides. For example, the condensation reaction of the reactive derivative of the compound (II) with the compound (III) or a salt thereof and the condensation reaction of the reactive derivative of the compound (IV) with the compound (V) or a salt thereof can be conducted either in the presence or absence of an acid acceptor in a solvent. Suitable examples of the acid acceptor include alkali metal hydroxides (e.g., potassium hydroxide, sodium hydroxide), alkali metal carbonates (e.g., sodium carbonate, potassium carbonate), alkali metal bicarbonates (e.g., sodium bicarbonate, potassium bicarbonate), trialkyl amines (e.g., trimethylamine, triethylamine), N,N-dialkylanilines (e.g., N,N-dimethylaniline, N,N-diethylaniline), pyridine, N-alkylmorpholines (e.g., N-methylmorpholine), and so forth. Dioxane, tetrahydrofuran, acetonitrile, methylene chloride, dimethylformamide, dimethylacetamide, ethyl acetate, pyridine, acetone and water are suitable as the solvent. It is preferred to carry out the reaction at a temperature of −50° to 50° C., especially at −15° to 5° C.

On the other hand, the condensation reaction of the compound (II) with the compound (III) or a salt thereof and the condensation reaction of the compound (IV) or a salt thereof with the compound (V) or a salt thereof can be conducted in the presence of a dehydrating agent in a solvent. Suitable examples of the dehydrating agent include dicyclohexylcarbodiimide, N-cyclohexyl-N'-morpholinocarbodiimide, N-ethyl-N'-(3-dimethylaminopropyl)carbodiimide, phosphorus oxychloride, phosphorus trichloride, thionyl chloride, oxalyl chloride, triphenylphosphine and the like. Vilsmeier reagent prepared from dimethylformamide and phosphorus oxychloride, from dimethylformamide and oxalyl chloride, from dimethylformamide and phosgen or from dimethylformamide and thionyl chloride may also be used as said dehydrating agent. It is preferred to carry out the reaction at a temperature of −50° to 50° C., especially at −20° to 0° C. −20° to 0° C. Dioxane, tetrahydrofuran, acetonitrile, chloroform, methylene chloride, dimethylformamide, N,N-dimethylacetamide, ethyl acetate, pyridine, acetone and water are suitable as the solvent.

[Reaction Step (C)]

The conversion of the compound (VI), a salt thereof or a reactive derivative thereof into the corresponding amide thereof can be conducted in a conventional manner, i.e., by treatment with ammonia or an ammonia-releasing substance. For example, this amidation is carried out by treating the compound (VI) or a salt thereof with ammonia or an ammonia-releasing substance in the presence of a dehydrating agent in a solvent. Any compounds which generate or release ammonia in the reaction solution may be used as the ammonia-releasing substance of the invention. Such ammonia-releasing substance includes, for example, ammonium chloride, ammonium carbonate and the like. The same dehydrating agents as mentioned in the reaction steps (A) and (B) may also be used in this step. It is preferred to carry out the reaction at a temperature of −20 to 20° C., especially at −5° to 5° C. Dimethylformamide, dimethylsulfoxide and tetrahydrofuran are suitable as the solvent.

The amidation is also carried out, for example, by treating the reactive derivative of the compound (VI) with ammonia or ammonia-releasing substance in the presence or absence of an acid acceptor in a solvent. The same acid acceptors as mentioned in the reaction steps (A) and (B) may also be used in this step. It is preferred to carry out the reaction at a temperature of −20° to 20° C. Methanol, ethanol, dimetylformamide and dimethylsulfoxide are suitable as the solvent.

[Reaction Step (D)]

When $X^1$ and/or $X^2$ of the product obtained in the step (A), (B) or (C) is (or are) the protecting group or groups, said protecting group or groups may be readily removed from the product in conventional manners. For example, the removal of the protecting group or groups may be conducted by hydrolysis, electrolysis, base treatment, acid treatment, reduction, oxidation or any combination thereof. More specifically, for example, when the protecting group is benzoyl, said group may be removed by treating the compound with a base. Suitable examples of such base include ammonia, mono- or di- lower alkyl amine (lower-alkyl group in this case is, for example, methyl, ethyl, isopropyl or n-butyl) and sodium alkoxide (e.g., sodium methoxide, sodium ethoxide). This reaction may be conducted with or without a solvent (e.g., methanol, ethanol). It is preferred to carry out the reaction at a temparature of −5° to 0° C. When the protecting group is benzoyl, acetyl, tert.-butoxycarbonyl, benzhydryl, trityl or p-nitrophenylsulphenyl, said group may be removed by treating the compound with an acid. Suitable examples of such acid include formic acid, trifluoroacetic acid, benzenesulfonic acid, p-toluensulfonic acid, hydrogen chloride or hydrogen bromide. This reaction may be conducted with or without a solvent (e.g., water, methanol, ethanol, acetic acid or dioxane). It is preferred to carry out the reaction at a temperature of −30° to 70° C. When the protecting group is benzyloxycarbonyl, p-methoxybenzyloxycarbonyl, benzyl or p-methoxybenzyl, the removal of said protecting group may be conducted by catalytic hydrogenation. This catalytic hydrogenation is preferably carried out at a temperature of 0° to 100° C., and preferred examples of the catalyst include palladium-BaCO$_3$, palladium-charcoal and palladium-black. Methanol, ethanol, tetrahydrofuran and water are suitable as the reaction solvent. When the protecting group is methoxycarbonyl or ethoxycarbonyl, said group may be removed by hydrolysis of the compound, or by base treatment. The hydrolysis can be carried out in conventional manners, for example, by treating it with a base such as potassium hydroxide, or an acid such as hydrochloric acid or hydrobromic acid. It is preferred to carry out said hydrolysis at a temperature of 0° to 70° C. When the protecting group is tosyl, said group may be removed by electrolysis, base treatment or treating with 1-hydroxybenzotriazole.

[Reaction Step (E)]

The product thus obtained in the above-mentioned reaction step and steps may be converted, if required, into an acid addition salt thereof by treating it with the stoichiometrically equimolar amount of an acid in accordance with conventional manners.

In the above-mentioned reactions, the starting compounds (II)–(VI) may be used in the form of either an optically active isomer or a mixture thereof. Since said reactions of the invention proceed without racemization, the compound (I) is readily obtained in the form of an optically active isomer by the use of the corresponding optically active isomers of the compounds (II)–(VI).

Among the starting compounds, the compound (II) may be prepared, for example, by reacting 4,5-dihydroorotic acid (J. Am. Chem. Soc., 75, 6086 (1953)) with benzyl halide in the presence of an acid acceptor (e.g., triethylamine) at −50° to 50° C., reacting the resulting benzyl 4,5-dihydroorotate with a methylating agent (e.g., methyl iodide)in the presence of an acid acceptor (e.g., sodium hydride) at −50° to 100° C., if required, introducing a protecting group into the thus-obtained benzyl 1-methyl-4,5-dihydroorotate at 3-position thereof and then subjecting the resulting product to catalytic hydrogenation to remove benzyl group therefrom.

The compound (IV) may be prepared by condensing the compound (II) with histidine or $N^{im}$-protected histidine according to a conventional method of peptide synthesis. The compound (VI) may be also prepared by condensing the compound (II) with histidyl-proline or the compound (IV) with proline according to a conventional method of peptide synthesis.

While the compound (I) of the present invention can exist in the form of eight optical isomers due to the three asymmetric carbon atoms involved therein, all of eight optical isomers or a mixture thereof are included within the scope of the invention. Among these isomers, however, (1-methyl-L-4,5-dihydroorotyl)-L-histidyl-L-prolinamide is especially preferred for medicinal use.

The compound (I) can be used for pharmaceutical use either as the free base or as an acid addition salt thereof. Pharmaceutically acceptable acid addition salts of the compound (I) are, for example, inorganic acid addition salts such as hydrochloride, hydrobromide, sulfate or nitrate; and organic acid addition salts such as acetate, maleate, tartrate, succinate, citrate, methanesulfonate, malate, oxalate or benzenesulfonate. The compound (I) or a pharmaceutically acceptable acid addition salt thereof may be administered either orally or parenterally. Further, the compound (I) or a salt thereof may be used in the form of a pharmaceutical preparation containing the same compound in conjunction or admixture with a pharmaceutical excipient suitable for oral or parenteral administration. Suitable excipients are, for example, starch, lactose, glucose, potassium phosphate, corn starch, arabic gum, stearic acid or other known medicinal excipients. The pharmaceutical preparation may be in solid form such as, for example, tablets, powders, capsules or granules; or in liquid form such as, for example, solutions or suspensions. Further, when administered parenterally, the pharmaceutical preparation may be used in the form of injections.

As mentioned hereinbefore, the compound (I) of the present invention has much stronger activating effects upon central nervous system (e.g., antagonistic effect on pentobarbital anesthesia, increasing effect on spontaneous locomotor activity, antagonistic effect on reserpine-induced hypothermia and potentiating effect on action of L-Dopa) with relatively less side effects (e.g., TSH-releasing activity) as compared with TRH or its derivatives disclosed in U.S. Pat. Nos. 4,100,152 and 4,045,556. Especially, the compound (I) is characteristic in that it shows excellent therapeutic activity even by oral administration, though TRH itself when administered orally shows no substantial therapeutic effects. Therefore, the compound (I) of the present invention is much more useful as palinesthesias, spontaneous movement stimulants or dopamine potentiators than TRH or its derivatives mentioned above. The compound (I) is also useful for the treatment or prophlaxis of central nervous system disorders such as, for example, consciousness disorders, short attention span, speech disorders, hypobulia, Lennox syndrome, senil dementia, hypnotic intoxication, autism, hyperkinesia, schizophrenia, depression and parkinsonism in a warm-blooded animal including human being.

Therapeutic dose of the compound (I) or its salt depends on route of administration; the age, weight and condition of patients; and the particular disease to be treated. In general, however, it may be used at a dose of 0.5 μg to 5 mg per kilogram of body weight per day; especially at a dose of 10 μg to 1 mg per kilogram of body weight per day in the case of oral administration; or at a dose of 1 μg to 100 μg per kilogram of body weight per day in the case of parenteral administration (e.g., intravenously, intramuscularly, subcutaneously).

Throughout the specification and claims, the terms "1-methyl-4,5-dihydroorotic acid" and "1-methyl-4,5-dihydroorotyl" mean 1-methyl-1,2,3,4,5,6-hexahydro-2,6-dioxo-4-pyrimidinecarboxylic acid and 1-methyl-1,2,3,4,5,6-hexahydro-2,6-dioxo-4-pyrimidinecarbonyl, respectively.

Practical and presently-preferred embodiments of the present invention are illustratively shown in the following Experiments and Examples, and the test compounds used in the following Experiments 1–4 are as follows:
Test compounds:

The compound of the present invention: (1-methyl-L-4,5-dihydroorotyl)-L-histidyl-L-prolinamide No. 1: (2,3,4,5-tetrahydro-2-oxo-L-5-furancarbonyl)-L-histidyl-L-prolinamide (U.S. Pat. No. 4,100,152)

No. 2: Orotyl-L-histidyl-L-prolinamide (U.S. Pat. No. 4,045,556).

Experiments 1

The pharmacological activities of test compounds estimated by oral administration.

(Methods)

(1) Antagonistic effect on reserpine-induced hypothermia

Male STD/ddY mice which showed the body temperatures of 30° C. or lower about 17 to 20 hours after subcutaneous administration of reserpine (3 mg/kg) were used in this experiments. A test compound dissolved in distilled water was orally administered to the mice, and the rectal temperature was measured 30, 60, 120, 180 and 300 minutes after the administration of the test compound. The increase in the body temperature of the medicated group of mice was compared with that of the control group of mice which received distilled water instead of the test compound solution.

(2) Increasing effect on spontaneous locomotor activity

Male STD/ddY mice were individually placed in Ambulometer (i.e., an apparatus for measuring spontaneous locomotor activity; manufactured by OHARA IKA Co.) for 30 minutes to acclimatize to the apparatus. Thereafter, a test compound dissolved in distilled water was orally administered to the mice and, immediately after administration of the test compound, the spontaneous locomotor activity was measured for 3 hours. Distilled water was administered to the control group of mice instead of the test compound solution.

(3) Antagonistic effect on pentobarbital anesthesia

A test compound dissolved in distilled water was orally administered to male STD/ddY mice. Fifteen minutes after the administration of the test compound, pentobarbital sodium was intraperitoneally administered to the mice at a dose of 55 mg/kg. The duration of anesthesia was measured as the time from the disappearance of righting reflex to the recovery thereof. Distilled water was administered to the control group of mice instead of the test compound solution.

(Results)

The results are shown in the following Tables 1 and Table 2.

TABLE 1

| | Potency ratio to TRH tartrate[a] | | |
|---|---|---|---|
| | The compound of the present invention | No. 1 | No. 2 |
| Antagonistic effect on reserpine-induced hypothermia | 91.3 | 3.4 | 13.0 |

Note:
[a]The therapeutic effect of TRH tartrate was taken as 1, and the potency ratio of each test compound to TRH tartrate was calculated by parallel line assay method.

TABLE 2

| | Minimum effective dose[B] (mg/kg) | |
|---|---|---|
| | The compound of the present invention | TRH tartrate |
| Antagonistic effect on pentobarbital anesthesia | 1 | >100 |
| Increasing effect on spontaneous locomotor activity | 10 | >100 |

Note:
[B]The minimum effective dose means a minimum dose which is necessary to produce a decrease in the duration of pentobarbital anesthesia or to produce a statistically significant increase in the spontaneous locomotor activity as compound with that of the control group of mice.

Experiments 2

The pharmacological activities of test compounds estimated by parenteral administration.

(Methods)

(1) Antagonistic effect on reserpine-induced hypothermia/and Increasing effect on spontaneous locomotor activity The experiments were carried out in the same manner as described in Experiment 1 except that a test compound dissolved in a physiological saline solution was administered intraperitoneally to mice and, in estimating the increasing effect on spontaneous locomotor activity, said spontaneous locomotor activity was measured for 60 minutes immediately after administration of the test compound.

(2) Antagonistic effect on pentobarbital anesthesia

Pentobarbital sodium was intraperitoneally administered to male STD/ddY mice at a dose of 55 mg/kg. Ten minutes after the administration of pentobarbital sodium, a test compound dissolved in a physiological saline solution was intravenously administered to the mice which had lost the righting reflex. The duration of anesthesia was measured as the time from the end of administration of the test compound until the righting reflex regained. A physiological saline solution was administered to the control group of mice instead of the test compound solution.

(3) Potentiating effect on action of Dopamine

Reserpine was subcutaneously administered to male STD/ddY mice at a dose of 3 mg/kg, and about 16 to 20 hours later, L-Dopa was intraperitoneally administered to the mice at a dose of 200 mg/kg. Thirty minutes after administration of L-Dopa, a test compound dissolved in a physiological saline solution was administered intraperitoneally to the mice (when TRH was used as the test compound, it was administered 45 minutes after administration of L-Dopa). Spontaneous locomotor activity was measured by ANIMEX (i.e., an apparatus for mesuring spontaneous locomotor activity; manufactured by FERAD Co.) for 15 minutes starting from one hour after administration of L-Dopa. A physiological saline solution was administered to the control group of mice instead of the test compound solution.

(Results)

The results are shown in the following Tables 3.

TABLE 3

| | Potency ratio to TRH[c] | | |
|---|---|---|---|
| | The compound of the present invention | No. 1 | No. 2 |
| Antagonistic effect on reserpine-induced hypothermia | 31.4 | 5.7 | 7.4 |
| Increasing effect on spontaneous locomotor activity | 27.4 | 3.5 | 3.8 |
| Antagonistic effect on pentobarbital anesthesia | 2.7 | 1.3 | 1.9 |
| Potentiating effect on action of Dopamine | 18.5 | 2.5 | 2.6 |

Note:
[c]The therapeutic effects of TRH was taken as 1, and the potency ratio of each test compound to TRH was calculated by parallel line assay method.

EXPERIMENT 3

(Method)

TSH-releasing activity (side effect)

A test compound dissolved in a 0.1% BSA (bovine serum albumin)-containing physiological saline solution was intravenously administered to male JCL:SD rats. Fifteen minutes after the administration, blood was taken from the abdominal aorta under anesthesia. Serum TSH levels were determined by the double-antibody radioimmunoassay method (Midgley et al., Endocrinology., 79, 10 (1966)). The BSA-containing physiological saline solution was administered to the control group of rats instead of the test compound solution.

(Result)

The results are shown in the following Table 4.

TABLE 4

| | Potency ratio to TRH[c] | | |
|---|---|---|---|
| | The compound of the present invention | No. 1 | No. 2 |
| TSH-releasing activity | 1/30 | 1/40[d] | 1/12–1/13[e] |

Note:
[c]The effect of TRH on TSH-releasing activity was taken as 1, and the potency ratio of each test compound to TRH was calculated by parallel line assay method.
[d]Published data (cf. Chemical & Pharmaceutical Bulletin, 28(6) 1667–1672 (1980))
[e]Published data (cf. Thyrotropin-Releasing Hormone, 327–340 (1983). Edited by Griffiths, E. C.; Bennet, G. W. Raven: New York, N.Y.

EXPERIMENT 4

(Method)

Acute toxicity

A test compound was intravenously administered to male STD/ddY mice and the acute toxicity (LD$_{50}$) thereof was determined from mortality of mice 24 hours after administration of the test compound.

(Result)

The results are shown in the following Table 5.

TABLE 5

| | The compound of the present invention | No. 1 | No. 2 | TRH |
|---|---|---|---|---|
| LD$_{50}$ (mg/kg, i.v.) | 1589 | — | 1200[d] | 1450[d] |

Note:
[d]Published data (cf. Brain Research Reviews., 4, 389, (1982))

EXAMPLE 1

1.03 g of 1-methyl-L-4,5-dihydroorotic acid and 760 mg of N-hydroxysuccinimide are dissolved in 20 ml of dimethylformamide, and 1.4 g of dicyclohexylcarbodiimide are added thereto at 0° C. The mixture is stirred at the same temperature for 1.5 hours. 2.8 g of L-histidyl-L-prolinamide dihydrobromide and 2 ml of triethylamine are added to the mixture under cooling, and the mixture is stirred at 0° to 15° C. for 2 days. Insoluble materials are filtered off, and the filtrate is concentrated under reduced pressure to remove dimethylformamide. The residue is dissolved in diluted hydrochloric acid, and insoluble materials are filtered off. The filtrate is washed with chloroform, alkalized with sodium bicarbonate and then passed through a column packed with styrene-divinylbenzene copolymer resin (manufactured by Mitsubishi Chemical Industries Ltd. under the trademark "MIC GEL CHP-20P"; hereinafter simply referred to as "CHP-20P resin"). After the column is washed with 300 ml of water, the desired product is eluted with water. The fractions which are positive to the Pauly's reaction are collected and lyophilized. The product thus obtained is crystallized with water and recrystallized from water. The crystals are dried at 60° C. under reduced pressure for 3 days. One g of (1-methyl-L-4,5-dihydroorotyl)-L-histidyl-L-prolinamide.½ H$_2$O is obtained.

M.p.: 158°–160° C. (decomp.).

$[\alpha]_D^{25}$: −16.4° (C=1, H$_2$O).

EXAMPLE 2

(1) 1.56 g of 1-methyl-L-4,5-dihydroorotic acid and 1.15 g of N-hydroxysuccinimide are dissolved in 30 ml of dimethylformamide, and 2.06 g of dicyclohexylcarbodiimide are added thereto at 0° C. The mixture is stirred at room temperature for 2 hours. The solution thus obtained is hereinafter referred to as "Solution A". On the other hand, 3.43 g of benzyl L-histidyl-L-prolinate.2HCl are dissolved in dimethylformamide, and 1.67 g of triethylamine are added thereto. The mixture is stirred at 0° C. for 20 minutes, and insoluble materials are filtered off. The filtrate is added to "Solution A", and the mixture is stirred at 0° C. for 4 hours and then at 10° C. for one day. Insoluble materials are filtered off, and the filtrate is concentrated under reduced pressure at 40° C. to remove dimethylformamide. The residue is dissolved in water, and insoluble materials are filtered off. The filtrate is adjusted to pH 8 with sodium bicarbonate and then passed through a column packed with CHP-20P resin. The column is washed with 500 ml of water, 500 ml of 20% methanol and 300 ml of 50% methanol, successively. Then, the desired product is eluted with 70% methanol. The fractions which are positive to the Pauly's reaction are collected from the eluate and concentrated under reduced pressure, whereby 3.65 g of benzyl (1-methyl-L-4,5-dihydroorotyl)-L-histidyl-L-prolinate are obtained as an oil.

IR$\nu_{max}^{chloroform}$ (cm$^{-1}$) 3300, 1725, 1680.

650 mg of the product obtained above are dissolved in 1 N-HCl and then lyophilized to give 690 mg of benzyl (1-methyl-L-4,5-dihydroorotyl)-L-histidyl-L-prolinate.HCl.H$_2$O as powder.

$[\alpha]_D^{22}$: −39.8° (C=0.5, H$_2$O).

IR$\nu_{max}^{nujol}$ (cm$^{-1}$): 1720, 1640–1680.

NMR (DMSO-d$_6$, δ): 1.7–2.4 (m, 4H), 2.90 (s, 3H), 2.4–3.9 (m, 6H), 3.9–4.2 (m, 1H), 4.3–4.5 (m, 1H), 4.6–5.0 (m, 1H), 5.09 (s, 2H), 7.2–7.5 (m, 5H), 8.96 (s, 1H).

Mass (m/e): 496 (M+).

(2) 700 mg of benzyl (1-methyl-L-4,5-dihydroorotyl)-L-histidyl-L-prolinate are dissolved in 20 ml of methanol, and 20 mg of palladium-black are added thereto. The mixture is stirred at room temperature for 3 hours in hydrogen gas. 20 ml of water are added to the reaction mixture, and the catalyst is filtered off. The filtrate is evaporated to remove solvent. The residue is crystallized with methanol, whereby 290 mg of (1-methyl-L-4,5-dihydroorotyl)-L-histidyl-L-proline.5/4 $H_2O$ are obtained.

M.p.: 233°–236° C. (decomp.).
$[\alpha]_D^{20}$: −17.2° (C=0.5, $H_2O$).
IR$\nu_{max}^{nujol}$ (cm$^{-1}$): 1715, 1680, 1630.
NMR ($D_2O$, δ): 1.7–2.4 (m, 4H), 2.6–3.9 (m, 6H), 3.03 (s, 3H), 4.0–4.45 (m, 2H), 4.95 (t, 1H), 7.27 (s, 1H), 8.57 (s, 1H).

(3) A mixture of 4.29 g of (1-methyl-L-4,5-dihydroorotyl)-L-histidyl-L-proline, 1.15 g of N-hydroxysuccinimide, 2.26 g of dicyclohexylcarbodiimide and 30 ml of dimethylformamide is stirred at 0° C. for 40 minutes and at room temperature for 80 minutes. 30 ml of 15% ammonia-methanol are then added to the mixture at 0° C., and the mixture is stirred at 0° C. for 30 minutes and at room temperature for one hour. Insoluble materials are filtered off, and the filtrate is evaporated to remove dimethylformamide. The residue is dissolved in 20 ml of water, and insoluble materials are again filtered off. The filtrate is adjusted to pH 8 with sodium bicarbonate and then passed through a column packed with CHP-20P resin. After the column is washed with 2 liters of water, the desired product is eluted with 10% methanol. The fractions which are positive to the Pauly's reaction are collected and concentrated under reduced pressure. The residue is dissolved in 10 ml of water, and allowed to stand in a refrigerator. Crystalline precipitates are collected by filtration, washed with water, and then dried at 25° C. for one day, whereby 3.3 g of (1-methyl-L-4,5-dihydroorotyl)-L-histidyl-L-prolinamide.7/2 $H_2O$ are obtained.

M.p.: 72°–75° C.
$[\alpha]_D^{25}$: −13.6° (C=1, $H_2O$).
IR$\nu_{max}^{nujol}$ (cm$^{-1}$): 3400, 3250, 1710, 1660, 1610, 1540.

EXAMPLE 3

(1) 900 mg of 3-benzoyl-1-methyl-L-4,5-dihydroorotic acid, 449 mg of N-hydroxysuccinimide and 782 mg of dicyclohexylcarbodiimide are dissolved in 13 ml of dimethylformamide, and the mixture is stirred at 0° C. for 40 minutes and then at room temperature for 80 minutes. The reaction mixture is cooled to −5° C., and 1.4 g of L-histidyl-L-prolinamide.2HBr and 0.94 ml of triethylamine are added thereto. The mixture is stirred at 0° C. for 3 hours and at 10° C. for one day. Insoluble materials are filtered off, and the filtrate is distilled to remove solvent. The residue is dissolved in 50 ml of 1% HCl and washed with chloroform. The water layer is adjusted to pH 8 with sodium bicarbonate and allowed to stand for one day in a refrigerator. The precipitates are collected by filtration, washed with water and then dried at 50° C., whereby 1.05 g of (3-benzoyl-1-methyl-L-4,5-dihydroorotyl)-L-histidyl-L-prolinamide are obtained.

M.p.: 228°–230° C. (decomp.).
$[\alpha]_D^{23}$: +27.2° (C=0.5, dimethylformamide).
IR$\nu_{max}^{nujol}$ (cm$^{-1}$): 3400, 3200, 1738, 1680, 1620.
NMR (DMSO-$d_6$, δ): 1.6–2.2 (m, 4H), 2.6–3.8 (m, 6H), 3.00 (s, 3H), 4.0–4.8 (m, 2H), 4.9–5.1 (m, 1H), 6.9–7.1 (m, 2H), 7.3–7.8 (m, 6H), 8.1 (br, 1H), 8.65 (br d, 1H).

(2) 510 mg of (3-benzoyl-1-methyl-L-4,5-dihydroorotyl)-L-histidyl-L-prolinamide Eare dissolved in 3 ml of methanol, and 136 mg of 15% ammonia - methanol are added thereto. The mixture is stirred at room temperature for minutes and distilled to remove methanol. 5 ml of water are added to the residue, and insoluble materials are filtered off. The water layer is washed with ethyl acetate, and is concentrated to one ml in volume. After the residue is allowed to stand for one day in a refrigerator, the crystalline precipitates are collected by filtration, washed with water and dried at 25° C. for one day. 400 mg of (1-methyl-L-4,5-dihydroorotyl)-L-histidyl-L-prolinamide.7/2 $H_2O$ are thereby obtained.

The physico-chemical properties of this product are identical with those of the sample obtained in Example 2-(3).

EXAMPLE 4

(1) 6.37 g of 1-methyl-L-4,5-dihydroorotic acid and 11.3 g of 95% pentachlorophenol are dissolved in 80 ml of dimethylformamide, 8.3 g of dicyclohexylcarbodiimide are added thereto at −5° to 0° C., and the mxture is stirred at the same temperature for one hour. 21.8 g of benzyl histidinate di-tosylate (Bull. Chem. Soc. Jap., 31, 784(1958)) and 75 mg of triethylamine are added thereto at −5° to 0° C. The mixture is stirred at 5° C. for 2 hours and at room temparature for one day. Insoluble materials are filtered off and the filtrate is concentrated under reduced pressure. The residue is dissolved in 80 ml of water, washed with 80 ml of ether and concentrated under reduced pressure. The residue is purified by silica gel column chromatography (solvent; chloroform : methanol=4:1), and is recrystallized from methanol. 6.0 g of benzyl (1-methyl-L-4,5-dihydroorotyl)-L-histidinate are obtained.

M.p.: 194°–195° C.
$[\alpha]_D^{21}$: +21.8° (C=0.5, dimethylformamide).
IR$\nu_{max}^{nujol}$ (cm$^{-1}$): 3300, 3200, 1735, 1710, 1660.

(2) 2.7 g of benzyl (1-methyl-L-4,5-dihydroorotyl)-L-histidinate are dissolved in 50 ml of water, and 50 ml of palladium-black are added thereto. The mixture is treated in the same manner as described in Example 2-(2), whereby 1.8 g of (1-methyl-L-4,5-dihydroorotyl)-L-histidine.½$H_2O$ are obtained as powder.

$[\alpha]_D^{21}$: +68.8° (C=0.5, $H_2O$).
IR$\nu_{max}^{nujol}$ (cm$^{-1}$): 1720, 1660.

(3) 1.23 g of dicyclohexylcarbodiimide are added to a mixture of 1.56 g of (1-methyl-L-4,5-dihydroorotyl)-L-histidine, 565 mg of N-hydroxysuccinimide and 15 ml of dimethylformamide at −10° to −5° C., and the mixture are stirred at the same temparature for 30 minutes. 570 mg of L-prolinamide are added thereto and the mixture is stirred at −5° to 0° C. for 2 hours and at room temperature for one day. After the reaction, insoluble materials are filtered off and washed with 50 ml of water. The filtrate and washings are combined and washed with chloroform. The solution is adjusted to pH 8 with sodium bicarbonate, and passed through a column packed with CHP-20P resin. The column is washed with 200 ml of water, and then the desired product is eluted with 20% methanol. The fractions which are positive to the Pauly's reaction are collected from the eluate and concentrated under reduced pressure. The residue is cooled, and crystalline precipitates are collected by filtration. 1.17 g of (1-methyl-L-4,5-dihydroorotyl)-L-histidyl-L-prolinamide.7/2 H$_2$O are obtained as crystal.

The physico-chemical properties of this product are identical with those of the sample obtained in Example 2-(3).

EXAMPLE 5

(1) 516 mg of 1-methyl-L-4,5-dihydroorotic acid and 345 mg of N-hydroxysuccinimide are dissolved in 9 ml of dimethylformamide, and 680 mg of dicyclohexylcarbodiimide are added thereto at 0° to 5° C. The mixture is stirred at the same temperature for 40 minutes and at room temperature for 80 minutes. 1.6 g of N$^{im}$-tosyl-L-histidyl-L-prolinamide trifluoroacetate (Bull. Chem. Soc. Jap., 49, 1595(1976)) and 0.5 ml of triethylamine added to the mixture and stirred at 10° C. for one day. After the reaction, the mixture is concentrated under reduced pressure, and the residue is dissolved in 30 ml of chloroform. Insoluble materials are filtered off, and the filtrate is washed with water and dried. After the mixture is concentrated under reduced pressure, the residue is purified by silica gel column chlomatography (solvent; chloroform:ethyl acetate:methanol=5:4:2). whereby 1.2 g of (1-methyl-L-4,5-dihydroorotyl)-n$^{im}$-tosyl-L-histidyl-L-prolinamide are obtained as powder.

$[\alpha]_D^{25}$: +8.3° (C=1, dimethylformamide).
IR$\nu_{max}^{nujol}$ (cm$^{-1}$): 1720, 1680, 1670, 1640.

(2) 1.2 g of (1-methyl-L-4,5-dihydroorotyl)-N$^{im}$-tosyl-L-histidyl-L-prolinamide are dissolved in 10 ml of 25% ammonia - methanol and allowed to stand at room temperature for one day. After the mixture is concentrated under reduced pressure, the residue is dissolved in 10 ml of water, and washed with chloroform. The aqueous solution is concentrated to 3 ml in volume and cooled. The crystalline preciptates are collected by filtration, washed with water and then dried, whereby 620 mg of (1-methyl-L-4,5-dihydroorotyl)-L-histidyl-L-prolinamide.7/2 H$_2$O are obtained.

The physico-chemical properties of this product are identical with those of the sample obtained in Example 2-(3).

EXAMPLE 6

(1) 1.24 g of dicyclohexylcarbodiimide are added to the mixture of 1.36 g of 3-tert.-butoxycarbonyl-1-methyl-DL-4,5-dihydroorotic acid, 690 mg of N-hydroxysuccinimide and 20 ml of dimethylformamide at 0° to 5° C. The mixture is stirred at room tempereture for 1.5 hours. 2.06 g of L-histidyl-L-prolinamide 2HBr and 1.7 ml of triethylamine are added to the reaction mixture at −5° to 0° C., and the mixture is stirred at 10° C. for one day. After insoluble materials are filtered off, the filtrate is concentrated under reduced pressure. 30 ml of an aqueous 20% citric acid solution are added to the residue and insoluble materials are filtered off. The filtrate is adjusted to pH 8 with sodium bicarbonate, and saturated with sodium chloride. Then, the filtrate is extracted with chloroform, and the extract is concentrated. The residue is crystallized with n-hexane and the crystalline precipitate are filtered, whereby 2.1 g of (3-tert.-butoxycarbonyl-1-methyl-DL-4,5-dihydroorotyl)-L-histidyl-L-prolinamide.4H$_2$O.½n-hexane are obtained.

M.p.: 80°–90° C.

$[\alpha]_D^{22}$: −16.8° (C=1, dimethylformamide).

(2) A mixture of 1 g of (3-tert.-butoxycarbonyl-1-methyl-DL-4,5-dihydroorotyl)-L-histidyl-L-prolinamide.4H$_2$O.½n-hexane and 3 ml of trifluoroacetic acid is stirred at room temperature for 30 minutes. The mixture is concentrated under reduced pressure to remove trifluoroacetic acid. The residue is dissolved in 20 ml of water and adjusted to pH 8 with sodium bicarbonate. The solution is introduced into the the column packed with CHP-20P resin. After the column is washed with 300 ml of water, the desired product is eluted with 20% methanol. The fractions which are positive to the Pauly's reaction are collected and lyophilized, whereby 560 mg of (1-methyl-DL-4,5-dihydroorotyl)-L-histidyl-L-prolinamide.H$_2$O are obtained.

$[\alpha]_D^{22}$: −65.6° (C=1, H$_2$O).
IR$_{max}^{nujol}$ (cm$^{-1}$): 3250, 1720, 1660.

Preparation 1

(1) 5.0 g of L-4,5-dihydroorotic acid (J. Am. Chem. Soc., 75, 6086(1953)) are suspended in 80 ml of dimethylformamide, and 4.4 ml of triethylamine and 3.76 ml of benzyl bromide are added thereto. The mixture is stirred at room temperature for 2 days. 6.6 ml of triethylamine and 3.76 ml of benzyl bromide are further added to the mixture, and the mixture is stirred at room temperature for 2 days. The mixture is concentrated under reduced pressure to remove solvent. Water is added to the residue, and the precipitated crystals are collected by filtration, washed with water and then recrystallized from methanol. 5.8 g of benzyl L-4,5-dihydroorotate are obtained.

M.p.: 187°–189° C.

$[\alpha]_D^{25}$: +56.3° (C=1, dimethylformamide).

(2) 6.6 g of benzyl L-4,5-dihydroorotate are dissolved in 66 ml of dimethylformamide, and 5 ml of methyl iodide are added thereto. 1.29 g of sodium hydride (62% oil dispersion) are added to the mixture at 22° to 28° C., and the mixture is stirred at about 25° C. for 40 minutes. Then, the mixture is adjusted to pH 4 with acetic acid, and then concentrated at a temperature below 40° C. under reduced pressure to remove dimethylformamide. Ethyl acetate is added to the residue, and the precipitated crystals are collected by filtration, washed with ethyl acetate and then dried. Water is added to the crystals, and the aqueous mixture is stirred for 20 minutes. The crystals are collected by filtration and then recrystallized from ethyl acetate. 3.25 g of benzyl 1-methyl-L-4,5-dihydroorotate are obtained.

M.p.: 162°–164° C.

$[\alpha]_D^{25}$: +51.7° (C=1, dimethylformamide).

(3) 4 g of benzyl 1-methyl-L-4,5-dihydroorotate are dissolved in 80 ml of tetrahydrofuran, and 340 ml of ethanol are added thereto. 0.4 g of 5% palladium-charcoal is added to the mixture, and the mixture is shaken at room temperature in hydrogen gas atmosphere under an atmospheric pressure. After the reaction is completed, insoluble materials are filtered off. The filtrate is concentrated under reduced pressure to dryness, and the residue is recrystallized from methanol. 1.9 g of 1-methyl-L-4,5-dihydroorotic acid are obtained.

M.p.: 214°–216° C.

$[\alpha]_D^{20}$: +49.2° (C=1, dimethylformamide).

This product can be used as the starting compound of Example 1.

Preparation 2

(1) 2.61 g of dicyclohexylcarbodiimide are added to a mixture of 5 g of N$^\alpha$-tert-butoxycarbonyl-N$^{im}$-tosyl-L-histidine, 2.94 g of benzyl L-prolinate HCl, 1.23 g of triethylamine and 50 ml of tetrahydrofuran. Said addition is carried out at 0° C., and the mixture is stirred at room temperature for one day. After the reaction, insoluble materials are filtered off, and the filtrate is evaporated to remove solvent. Ethyl acetate is added to the residue, and the mixture is washed with 1N-sulfuric acid, an aqueous saturated sodium bicarbonate solution and a saline solution, successively. Ethyl acetate layer is dried and evaporated to remove solvent. The residue is introduced into a silica gel column. After the column is washed with ether, the desired product is eluted with ethyl acetate. The eluate is condensed to dryness, whereby 6.0 g of benzyl (N$^\alpha$-tert-butoxycarbonyl-N$^{im}$-tosyl-L-histidyl)-L-prolinate are obtained as an oil.

(2) 6.0 g of benzyl (N$^\alpha$-tert.-butoxycarbonyl-N$^{im}$-tosyl-L-histidyl)-L-prolinate are dissolved in 50 ml of tetrahydrofuran, and 4.1 g of 1-hydroxybenzotriazole are added thereto. The mixture is stirred at room temperature for 4 hours. After the reaction, the mixture is evaporated to remove solvent, and ethyl acetate and 1N-sulfuric acid are added to the residue. After insoluble materials are filtered off, the aqueous layer is separated from the filtrate, adjusted to pH 8 with sodium bicarbonate and extracted with ethyl acetate. The extract is dried and then evaporated to remove solvent. The residue thus obtained is purified by silica gel column chromatography (solvent; chloroform:methanol=9:1), whereby 4.5 g of benzyl (N$^\alpha$-tert-butoxycarbonyl-L-histidyl)-L-prolinate are obtained as an oil.

IR$\nu_{max}^{chloroform}$ (cm$^{-1}$): 3400, 3300.

(3) 4.5 g of benzyl (N$^\alpha$-tert-butoxycarbonyl-L-histidyl)-L-prolinate are dissolved in 40 ml of 15% HCl - dioxane, and the mixture is stirred at room temperature for 30 minutes. The reaction mixture is evaporated to remove solvent, and diisopropylether is added to the residue. Precipitated powder is collected by filtration, washed with diisopropylether and dried under reduced pressure, whereby 4.0 g of benzyl L-histidyl-L-prolinate.2HCl(yield: quantitative ) are obtained. This product can be used as the starting compound of Example 2 without purification.

Preparation 3

(1) 2.62 g of benzyl 1-methyl-L-4,5-dihydroorotate and 10 g of triethylamine are suspended in 25 ml of dioxane. 2.81 g of benzoyl chloride are added dropwise to the suspension at room temperature, and the mixture is stirred at 60° to 65° C. for 3 hours. After the reaction mixture is evaporated to remove solvent, chloroform is added to the residue and the mixture is washed with water. The mixture is purified by silica gel chromatography (solvent; chloroform) and evaporated to remove solvent. The residue is recrystallized from ethyl acetate - n-hexane (1:1), whereby 1.6 g of benzyl 3-benzoyl-1-methyl-L-4,5-dihydroorotate are obtained.

M.p.: 110°–111° C.

[α]$_D^{25}$: +63.0° (C=0.5, methanol).

(2) 150 mg of 10% palladium-charcoal and 30 ml of ethanol are added to 1.5 g of benzyl 3-benzoyl-1-methyl-L-4,5-dihydroorotate, and the mixture is stirred at room temperature for 40 minutes in hydrogen gas. After the catalyst is filtered off, the filtrate is distilled to remove solvent. The residue is crystallized with n-hexane and is recrystallized from ethyl acetate - n-hexane (5:1), whereby 850 mg of 3-benzoyl-1-methyl-L-4,5-dihydroorotic acid are obtained.

M.p.: 185°–187° C.

[α]$_D^{24}$: +95.2° (C=0.5, methanol).

This product can be used as the starting compound of Example 3.

Preparation 4

(1) A mixture of 1.31 g of benzyl 1-methyl-DL-4,5-dihydroorotate, 1.2 g of di-tert.-butyl dicarbonate, 0.7 ml of triethylamine, 0.06 g of 4,4-dimethylaminopyridine, 1.7 ml of tetrahydrofuran and 3 ml of dimethylformamide is stirred at 25° to 27° C. for 2 hours. The reaction mixture is concentrated under reduced pressure. The residue is dissolved in 30 ml of ethyl acetate, and washed with water and an aqueous 10% citric acid solution. Then, the solution is dried and evaporated to remove solvent, and the residue is crystallized with ether - n-hexane, whereby 0.7 g of benzyl 3-tert.-butoxycarbonyl-1-methyl-DL-4,5-dihydroorotate are obtained.

M.p.: 157°–159° C.

IR$\nu_{max}^{nujol}$ (cm$^{-1}$): 1760, 1745, 1695.

(2) A mixture of 600 mg of benzyl 3-tert.-butoxycarbonyl-1-methyl-DL-4,5-dihydroorotate, 200 mg of 10% palladium-charcoal and 30 ml of methanol is shaken at room temperature in hydrogen gas atmosphere under an atmospheric pressure for 3 hours. After the reaction, insolbule materials are filtered off, and the filtrate is concentrated under reduced pressure. The residue is recrystallized from ethyl acetate - n-hexane, whereby 400 mg of 3-tert.-butoxycarbonyl-1-methyl-DL-4,5-dihydroorotic acid are obtained.

M.p.: 129°–130° C.

IR$\nu_{max}^{nujol}$ (cm$^{-1}$): 1795, 1740, 1725, 1675.

This product can be used as the starting compound of Example 6.

What we claim is:

1. 1-Methyl-4,5-dihydroorotyl-histidyl-prolinamide of the formula:

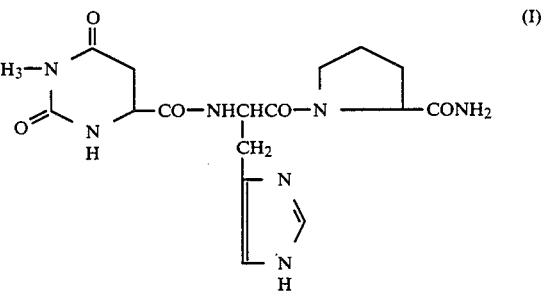

or a pharmaceutically acceptable acid addition salt thereof.

2. The compound claimed in claim 1, which is (1-methyl-L-4,5-dihydrooroty)-L-histidyl-L-prolinamide or a pharmaceutically acceptable acid addition salt thereof.

3. A pharmaceutical composition for treatment or prophylaxis of a central nervous system disorder, wherein the central nervous system disorder is consciousness disorders, short attention span, speech disorders, hypobulia, Lennox syndrome, senile dementia, hypnotic intoxication, autism, hyperkinesia, schizophrenia, depression or Parkinsonism, which comprises a therapeutically effective amount of the compound claimed in claim 1 or a pharmaceutically acceptable acid addition salt thereof and a pharmaceutically acceptable carrier therefor.

4. A method for treatment or prophylaxis of a central nervous system disorder in a warm-blooded animal, wherein the central nervous system disorder is consciousness disorders, short attention span, speech disorders, hypobulia, Lennox syndrome, senile dementia, hypnotic intoxication, autism, hyperkinesia, schizophrenia, depression or Parkinsonism, which comprises administering to said warm-blooded animal a therapeutically or prophylactically effective amount of the compound claimed in claim 1 or a pharmaceutically acceptable acid addition salt thereof.

5. A pharmaceutical composition for treatment or prophylaxis of a central nervous system disorder, wherein the central nervous system disorder is consciousness disorders, short attention span, speech disorders, hypobulia, Lennox syndrome, senile dementia, hypnotic intoxication, autism, hyperkinesia, schizophrenia, depression or Parkinsonism, which comprises a therapeutically effective amount of the compound claimed in claim 2 or a pharmaceutically acceptable acid addition salt thereof and a pharmaceutically acceptable carrier thereof.

6. A method for treatment or prophylaxis of a central nervous system disorder, wherein the central nervous system disorder is consciousness disorders, short attention span, speech disorders, hypobulia, Lennox syndrome, senile dementia, hypnotic intoxication, autism, hyperkinesia, schizophrenia, depression or Parkinsonism, which comprises administering to said warm-blooded animal a therapeutically or prophylactically effective amount of the compound claimed in claim 2, or a pharmaceutically acceptable acid addition salt thereof.

* * * * *